United States Patent
Jiang et al.

(10) Patent No.: US 11,221,437 B2
(45) Date of Patent: Jan. 11, 2022

(54) PROTEIN-MATRIX MICROLENS ARRAY DIFFRACTION DEVICE AND METHOD FOR PREPARING THE SAME

(71) Applicant: Tsinghua University, Beijing (CN)

(72) Inventors: Lan Jiang, Beijing (CN); Jianfeng Yan, Beijing (CN); Jiachen Yu, Beijing (CN)

(73) Assignee: TSINGHUA UNIVERSITY, Beijing (CN)

( * ) Notice: Subject to any disclaimer, the term of this patent is extended or adjusted under 35 U.S.C. 154(b) by 0 days.

(21) Appl. No.: 17/323,415

(22) Filed: May 18, 2021

(65) Prior Publication Data

US 2021/0341655 A1 Nov. 4, 2021

Related U.S. Application Data

(63) Continuation of application No. PCT/CN2020/109237, filed on Aug. 14, 2020.

(30) Foreign Application Priority Data

Sep. 18, 2019 (CN) .......................... 201910881861.8

(51) Int. Cl.
*C30B 7/04* (2006.01)
*G02B 5/18* (2006.01)
(Continued)

(52) U.S. Cl.
CPC .............. *G02B 5/1866* (2013.01); *C30B 7/04* (2013.01); *G02B 1/04* (2013.01); *G02B 5/1852* (2013.01);
(Continued)

(58) Field of Classification Search
CPC ......... C30B 7/04; C30B 29/56; G02B 5/1866; G02B 5/1852; G02B 1/04; C07K 1/14; C07K 299/00; G01N 21/718
See application file for complete search history.

(56) References Cited

U.S. PATENT DOCUMENTS

| 8,568,962 B2 * | 10/2013 | Hermans | G03F 7/36 430/321 |
| 9,903,819 B2 * | 2/2018 | Kjaerulff | G02B 27/0905 |

(Continued)

FOREIGN PATENT DOCUMENTS

| CN | 102608032 | 7/2012 |
| CN | 104923919 | 9/2015 |

(Continued)

OTHER PUBLICATIONS

Yao et al "Refractive micro lens array mode of dichromate gelatin with gray tone photolithograpghy" Microelectronic Engineering vol. 57-58 2001 pp. 729-735.*

(Continued)

*Primary Examiner* — Robert M Kunemund
(74) *Attorney, Agent, or Firm* — Hodgson Russ LLP

(57) ABSTRACT

Provided are a protein-matrix microlens array diffraction device and a preparation method thereof. The protein-matrix microlens array diffraction device includes a matrix of a protein crystal. A largest side of the protein crystal has a length of 100 to 500 μm, a surface of the protein crystal where the largest side is located is processed to have an array of microlens-like protrusions, a distance p between two adjacent microlens-like protrusions of the array of microlens-like protrusions is in a range of 10 to 100 μm, a diameter d of the microlens-like protrusion is in a range of 2 to 10 μm, and a height h of the microlens-like protrusion is in a range of 0.05 to 2 μm.

7 Claims, 2 Drawing Sheets

(51) Int. Cl.
  *G02B 1/04* (2006.01)
  *C07K 1/14* (2006.01)
  *G01N 21/71* (2006.01)

(52) U.S. Cl.
  CPC ............ *C07K 1/14* (2013.01); *C07K 2299/00* (2013.01); *G01N 21/718* (2013.01)

(56) References Cited

U.S. PATENT DOCUMENTS

| | | | |
|---|---|---|---|
| 2003/0032046 A1 | 2/2003 | Duffy et al. | |
| 2009/0020924 A1* | 1/2009 | Lin | B81C 1/00031 264/605 |
| 2009/0073569 A1* | 3/2009 | Jiang | A61B 1/05 359/626 |
| 2011/0104445 A1* | 5/2011 | Hermans | G03F 7/027 428/156 |
| 2018/0243952 A1* | 8/2018 | Okano | B29C 41/42 |

FOREIGN PATENT DOCUMENTS

| | | |
|---|---|---|
| CN | 106932843 | 7/2017 |
| CN | 108318485 | 7/2018 |
| CN | 109633795 | 4/2019 |
| CN | 109810167 | 5/2019 |
| CN | 110238530 | 9/2019 |
| CN | 110703372 | 1/2020 |
| WO | 2008118211 | 10/2008 |
| WO | 2010126640 | 11/2010 |

OTHER PUBLICATIONS

Sun et al "Dynamically tunable protein microlenses". Angewandte . Communication Angew. Chem. Int. Ed. 2012, 51, 1558-1562.*
Antonov, "Fabrication of microlenses in Ag-doped glasses by a focused continuous wave laser beam," Journal of Applied Physics, 2003, vol. 93, pp. 2343-2348.
WIPO, International Search Report and Written Opinion for PCT/CN2020/109237, dated Oct. 28, 2020.
SIPO, First Office Action for CN Application No. 201910881861.8, dated May 25, 2020.
Sun, "Study on Femtosecond Laser Direct Writing and Characteristics of Micro-Nano Photonic Devices in Protein," Information Science and Technology Series of Full-text Database of Chinese Doctoral Dissertation, 2015, No. 8, pp. 21-23.
SIPO, Second Office Action for CN Application No. 201910881861.8, dated Nov. 20, 2020.
Liu et al., "3D femtosecond laser patterning of collagen for directed cell attachment," Biomaterials, 2005, vol. 26, No. 22, pp. 4597-4605.
Vorobyev et al., "Direct femtosecond laser surface nano/microstructuring and its applications," Laser & Photonics Reviews, 2013, vol. 7, No. 3, pp. 385-407.
SIPO, Notification to Grant Patent Right for Invention for CN Application No. 201910881861.8, dated Mar. 4, 2021.
Sun et al., "Protein Functional Devices Manufactured by Femtosecond Laser Direct Writing," Laser & Optoelectronics Progress, 2013, pp. 080003-1-16.

* cited by examiner

PROTEIN-MATRIX MICROLENS ARRAY DIFFRACTION DEVICE AND METHOD FOR PREPARING THE SAME

CROSS-REFERENCE TO RELATED APPLICATION

This application is a continuation of International Application No. PCT/CN2020/109237, filed with the National Intellectual Property Administration of P. R. China on Aug. 14, 2020, claims priority to and benefits of Chinese Patent Application Serial No. 201910881861.8, filed with the National Intellectual Property Administration of P. R. China on Sep. 18, 2019, the entire contents of which are incorporated by reference herein.

FIELD

The present disclosure relates to the field of biological detection devices, and more particularly to a protein-matrix microlens array diffraction device and a method for preparing a protein-matrix microlens array diffraction device.

BACKGROUND

Protein molecules have a hierarchical structure that, when affected by factors such as an external temperature, and other molecules or ions in the environment, causes the protein molecules to be changed in molecular structure, physical and chemical properties. A microstructure or a device based on protein may be able to respond to the environment and thus may be applied in the field of biosensors. Optical waveguide of the protein served as a matrix may respond to the environment, resulting in a change of optical properties of the optical waveguide, for example, a light intensity output by the optical waveguide, thus realizing the detection of environment parameters, e.g., pH.

However, in existing technologies, only the light intensity is used as a measurable parameter, the measurement is performed in fewer dimensions, requirements for the sensor are strict, and the measurement/detection is easily interfered by various factors. Moreover, amorphous protein has poor stability in the environment and is easily degraded. In addition, the processing of protein-based microdevices is inherently difficult due to the sensitivity of protein materials to environmental temperature and other factors.

SUMMARY

Embodiments of the present disclosure seek to solve at least one of the problems existing in the related art to at least some extent.

In an aspect, the present disclosure provides in embodiments a protein-matrix microlens array diffraction device, characterized in that the protein-matrix microlens array diffraction device comprises a matrix of a protein crystal, a largest side of the protein crystal has a length L of 100 to 500 μm, a surface of the protein crystal where the largest side is located is processed to have an array of microlens-like protrusions, a distance p between two adjacent microlens-like protrusions of the array of microlens-like protrusions is in a range of 10 to 100 μm, a diameter d of the microlens-like protrusion is in a range of 2 to 10 μm, and a height h of the microlens-like protrusion is in a range of 0.05 to 2 μm.

In another aspect, the present disclosure provides in embodiments A method for preparing a protein-matrix microlens array diffraction device, comprising the following steps:

(1) preparing a protein crystal, comprising:
(1-1) mixing a protein solid with a solution having a concentration of a salt, comprising sodium chloride and sodium acetate, of 2% to 5% by mass to obtain a protein solution, wherein a mass fraction of the protein in the protein solution is 1 to 3 times a mass fraction of a saturated solution, and the protein solution is adjusted to have a pH of 4 to 6; and
(1-2) placing the protein solution obtained from step (1-1) in a container and leaving the protein solution to stand at a room temperature for a period of 6 to 24 h, during the period water of the protein solution is naturally evaporated, thereby obtaining the protein crystal, and
(2) emitting a femtosecond laser on a surface of the protein crystal obtained in step (1), wherein the femtosecond laser has a pulse duration of 35 to 120 fs, a single pulse energy of the femtosecond laser is half of a protein ablation threshold, and the femtosecond laser has a repetition frequency of 1 to 1000 Hz.

BRIEF DESCRIPTION OF THE DRAWINGS

These and other aspects and advantages of embodiments of the present disclosure will become apparent and more readily appreciated from the following descriptions made with reference to the drawings, in which.

DETAILED DESCRIPTION

Reference will be made in detail to embodiments of the present disclosure. The embodiments described herein with reference to drawings are explanatory, illustrative, and used to generally understand the present disclosure. The embodiments shall not be construed to limit the present disclosure.

Figure 1:
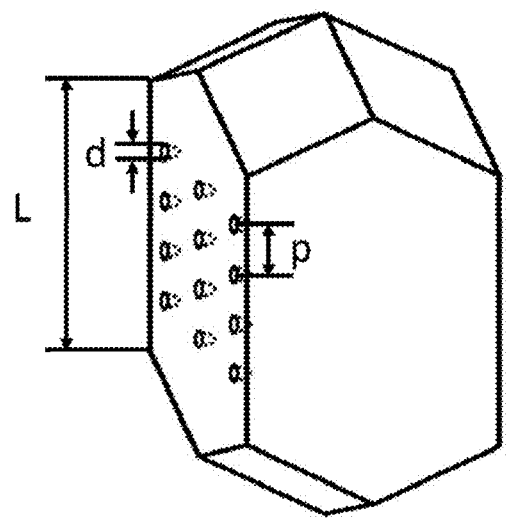
FIG. 1 is a schematic diagram showing a protein-matrix microlens array diffraction device according to an embodiment of the present disclosure.

The present disclosure provides in embodiments a protein-matrix microlens array diffraction device having a structure as shown in FIG. 1. A matrix of the protein-matrix microlens array diffraction device is a protein crystal, a largest side of the protein crystal has a length L of 100 to 500 μm, a surface of the protein crystal where the largest side is located is processed to have an array of microlens-like protrusions, a distance p between two adjacent microlens-like protrusions of the array of microlens-like protrusions is in a range of 10 to 100 μm, a diameter d of the microlens-like protrusion is in a range of 2 to 10 μm, and a height h of the microlens-like protrusion is in a range of 0.05 to 2 μm.

The present disclosure provides in embodiments a method for preparing a protein-matrix microlens array diffraction device, including the following steps.

In step 101, a protein crystal is prepared.

Specifically, a protein solid is mixed with a salt solution having a concentration of 2% to 5% by mass, to obtain a protein solution. The protein solution is adjusted to have a pH of 4 to 6. The salt solution may be a sodium chloride solution and/or a sodium acetate solution. A mass fraction of the protein in the protein solution is 1 to 3 times a mass fraction of a saturated protein solution, that is, the protein solution obtained is a supersaturated solution. In an example, saturated solution of hen egg white lysozyme (HEWL), a sample protein, has a concentration of 16 mg/mL. The supersaturated HEWL solution obtained in this method includes 16-48 mg/mL HEWL powder. The protein solution prepared may be placed in a container and stand at a room temperature for a period of 6 to 24 h. During this period, water of the protein solution is naturally evaporated, thereby obtaining the protein crystal.

In step 102, a femtosecond laser is emitted on a surface of the obtained protein crystal.

The femtosecond laser has a pulse duration of 35 to 120 fs. A single pulse energy of the femtosecond laser is less than a protein ablation threshold, but is enough to modify the protein to form micro-protrusions. A ratio of the single pulse energy to the protein ablation threshold may be in a range of 0.5 to less than 1. The femtosecond laser has a repetition frequency of 1 to 1000 Hz. The femtosecond laser single pulse energy is controlled by an attenuator in a processing optical path. Moreover, by controlling a shutter and a translation stage in the processing optical path, the femtosecond laser is focused on positions where microlenses to be processed are located. These microlenses will be periodically arranged. On this basis, the microlens-shaped protrusions can be processed one by one to form the microlens array diffraction device.

The protein-matrix microlens array diffraction device and the preparation method thereof provided by the present disclosure have the following advantages.

The protein-matrix microlens array diffraction device of the present application may be used as a biological detection device, and has unique response characteristics and good biocompatibility. Compared with existing detections using biological materials, for example, a biological detection realized by detecting light intensity output by the optical waveguide of the protein matrix, the protein-matrix microlens array diffraction device is able to convert measurement quantities into physical quantities such as shape, distribution, spacing distance of the diffraction pattern that are easier to measure, thus improving the detection accuracy and flexibility.

With the method for preparing a protein-matrix microlens array diffraction device of the present disclosure, single crystal of the protein is used as the matrix of the microlens array diffraction device, which is more stable in a solution environment, has a longer service life and a wider application range. Moreover, the present method applies the femtosecond laser to directly form micro-protrusions, which is easy to process and reduces the thermal damage.

The present disclosure is further described in detail with reference to the drawings as follows.

Figure 2:
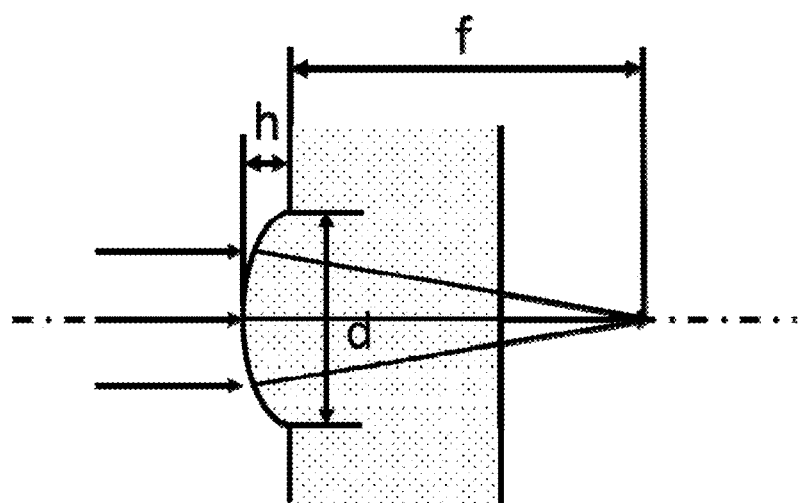
FIG. 2 is a schematic diagram showing a microlens according to an embodiment of the present disclosure.

FIG. 1 is a schematic diagram showing a protein-matrix microlens array diffraction device according to an embodiment of the present disclosure. The protein-matrix microlens array diffraction device has a matrix of a protein crystal, a largest side of the protein crystal has a length L of 100 to 500 µm, a surface of the protein crystal where the largest side is located is processed to have an array of microlens-like protrusions, a distance p between two adjacent microlens-like protrusions of the array of microlens-like protrusions is in a range of 10 to 100 µm. FIG. 2 is a schematic diagram showing a microlens according to an embodiment of the present disclosure. As shown in this enlarged diagram (a dash area refers to the protein), a diameter d of the microlens-like protrusion is in a range of 2 to 10 µm, and a height h of the microlens-like protrusion is in a range of 0.05 to 2 µm. In FIG. 2, arrows show a light direction. The parallel incident light can be focused through the curved surface. Based on the geometric relationship, a focal length f of the microlens may be calculated according to formula (1), where n represents a refractive index of the protein crystal.

$$f = \frac{h^2 + d^2/4}{2h(n-1)} \qquad (1)$$

Figure 3:
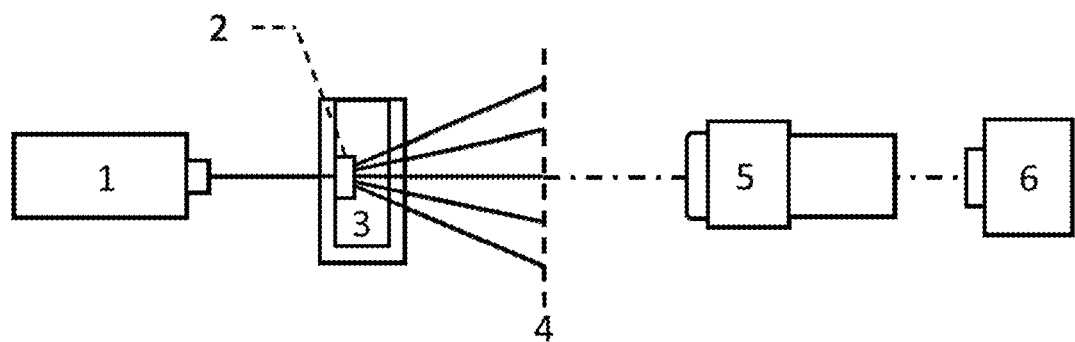
FIG. 3 is a schematic diagram showing an operation state of a protein-matrix microlens array diffraction device according to an embodiment of the present disclosure.

A verification optical path of the protein-matrix microlens array diffraction device of the present disclosure is shown in FIG. 3. When a laser beam is emitted perpendicularly to the surface of the crystal provided with the microlens array, a diffraction pattern is obtained on the back focal plane of the microlens. For diffraction patterns of different environmental solutions, position, shape, and intensity distribution of the diffraction pattern are related to shape and optical property of the protein and the environment. These parameters may be affected by solution molecules/ions concentration of the environment. On this basis, the detection of a concentration of molecules and ions in different solutions can be achieved.

The present disclosure provides in embodiments a method for preparing a protein-matrix microlens array diffraction device, including the following steps.

A protein crystal is prepared. A protein solid is mixed with a salt solution having a concentration of 2% to 5% by mass to obtain a protein solution. A mass fraction of the protein in the protein solution is 1 to 3 times a mass fraction of a saturated protein solution. The protein solution is adjusted to have a pH of 4 to 6. The protein solution prepared may be placed in a container and stand at a room temperature for a period of 6 to 24 h. During this period, water of the protein solution is naturally evaporated, thereby obtaining the protein crystal.

A femtosecond laser is emitted to a surface of the obtained protein crystal. The femtosecond laser has a pulse duration of 35 to 120 fs. A single pulse energy of the femtosecond laser is less than a protein ablation threshold, but is enough to modify the protein to form micro-protrusions. A ratio of the single pulse energy to the protein ablation threshold may be in a range of 0.5 to less than 1. The femtosecond laser has a repetition frequency of 1 to 1000 Hz. The femtosecond laser single pulse energy is controlled by an attenuator in a processing optical path. Moreover, by controlling a shutter and a translation stage in the processing optical path, the femtosecond laser is focused on positions where microlenses to be processed are located. These microlenses will be periodically arranged. On this basis, the microlens-shaped protrusions can be processed one by one to form the microlens array diffraction device.

In an embodiment, a salt of the salt solution may be selected from sodium chloride and sodium acetate.

The present disclosure is further described in detail with reference to the embodiments as follows.

In an embodiment, a hen egg white lysozyme (HEWL) crystal is used, a microlens array is processed on a surface of the protein crystal, and a structure of a device is shown in FIG. 1. The protein crystal is the HEWL crystal cultured by a common crystallization method, a largest side of which has a length L of 100 to 500 µm. A distance between two adjacent microlens-like protrusions of the microlens array is 10 μm. Moreover, the microlens has a diameter d of 3 μm and a height of 1 μm observed by an atomic force microscope.

The femtosecond laser used in the present disclosure is a titanium sapphire femtosecond laser from Coherent, with a center wavelength of 800 nm and a pulse width of <35 fs.

Example 1

A protrusion-shaped microlens array with a pitch of 10 μm is prepared on a surface of a protein crystal.

(1-1) In this example, HEWL is used as a protein raw material, and the supersaturated solution includes HEWL powder of 30 mg/ml, sodium chloride of 2.5% by mass and sodium acetate trihydrate of 1.36% by mass.

(1-2) 3 ml of the solution prepared in (1-1) is added into a transparent cuvette, and water is naturally evaporated at a temperature of 23° C. and a relative humidity of 30% for 24 h. A protein crystal with a largest side of about 100 to 500 μm in length is observed on a wall of the transparent cuvette.

(2-1) The femtosecond laser is emitted to a surface of the transparent cuvette containing the protein crystal, and is further focused on a surface of the protein crystal parallel to the surface of the transparent cuvette through a 10× objective lens. With an attenuator in the optical path, the laser energy can be controlled. Moreover, whether the laser is incident to the surface may be controlled by opening and closing a shutter in the optical path. The shutter is open, the femtosecond laser with a single pulse energy of 100 nJ is focused to process the surface of the protein crystal to form an ablation pit. Position of the ablation pit is marked as a position of a focus point of the laser.

(2-2) The femtosecond laser with a center wavelength of 800 nm and a pulse duration of 35 fs is used to modify the protein and produce the micro-protrusions. A ratio of a single pulse energy of the femtosecond laser to the ablation threshold is in a range of 0.5 to less than 1. For the HEWL, a single pulse ablation threshold is 80 nJ. In this case, the single pulse energy of the femtosecond laser is selected to be 40 nJ. Moreover, a repetition frequency is 1000 Hz, and the number of pulses is 100 (achieved by controlling an open time of the shutter to be 0.1 s). The single pulse energy is adjusted to 40 nJ by controlling the attenuator, and the shutter is closed after open for 0.1 s, thereby obtaining the micro-protrusion structure.

(2-3) By controlling the translation stage and the shutter, each time the protein crystal is moved for 10 μm to move the focus point position of the laser to a next point to be processed. Operations in step (2-2) are repeated to process each and every micro-protrusion, thus realizing the formation of the microlens array diffraction device. The prepared protrusions-shaped microlens array with a pitch of 10 μm is shown in FIG. 4(a).

Figure 4A:
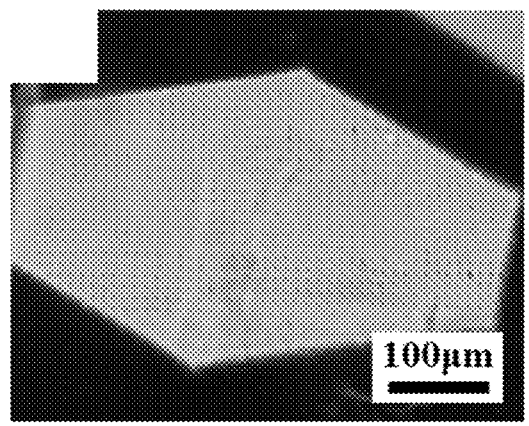
FIG. 4(a) is a diagram of a protein-matrix microlens array diffraction device according to an embodiment of the present disclosure.

The verification optical path of the protein-matrix microlens array diffraction device shown in FIG. 4(a) is illustrated in FIG. 3 (1: a continuous laser with a wavelength of 650 nm used as the light source for diffraction, 2: the protein-matrix microlens array diffraction device obtained by the above process, 3: a transparent cuvette containing a solution to be tested, 4: a back focal plane of the microlens, 5: a lens barrel with an adjustable focal length, and 6: CCD). The laser light passes through the protein-matrix microlens array diffraction device 2 to form the diffraction pattern on the back focal plane. The lens barrel 5 and the CCD 6 form an imaging system.

Figure 4B:
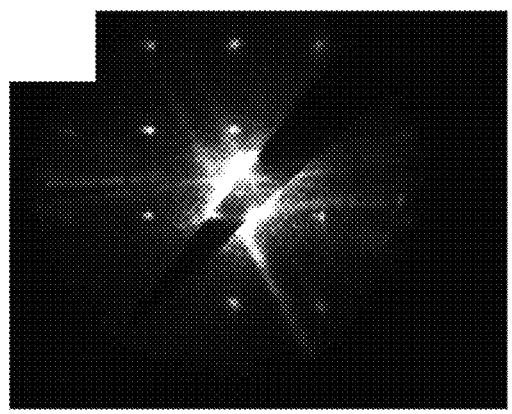
FIG. 4(b) is a diagram of a diffraction pattern formed by a microlens array diffraction device used for testing a solution.

A liquid is added to the transparent cuvette 3 with the above-mentioned protein-matrix microlens array diffraction device on the side wall. The liquid in this example includes sodium chloride of 2.5% by mass and sodium acetate trihydrate 1.36% by mass. The continuous laser 1 is turned on and the laser light passes through the microlens array diffraction device 2 to obtain a diffraction image on the back focal plane 4 of the microlens. The lens barrel 5 with the adjustable focal length is adjusted, such that the image on the focal plane 4 is imaged on the CCD 6 through the lens barrel 5. The diffraction pattern formed by the microlens array diffraction device in the liquid environment is recorded as shown in FIG. 4B.

Reference throughout this specification to "an embodiment," "some embodiments," "one embodiment", "another example," "an example," "a specific example," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example," "in an example," "in a specific example," or "in some examples," in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A protein-matrix microlens array diffraction device, characterized in that the protein-matrix microlens array diffraction device comprises a matrix of a protein crystal,
   a largest side of the protein crystal has a length of 100 to 500 μm,
   a surface of the protein crystal where the largest side is located is processed to have an array of microlens-like protrusions,
   a distance p between two adjacent microlens-like protrusions of the array of microlens-like protrusions is in a range of 10 to 100 μm,
   a diameter d of the microlens-like protrusion is in a range of 2 to 10 μm, and
   a height h of the microlens-like protrusion is in a range of 0.05 to 2 μm.

2. The protein-matrix microlens array diffraction device according to claim 1, wherein the protein crystal is an HEWL crystal.

3. The protein-matrix microlens array diffraction device according to claim 1, wherein the distance p between two adjacent microlens-like protrusions of the array of microlens-like protrusions is 10 μm.

4. The protein-matrix microlens array diffraction device according to claim 1, wherein the diameter d of the microlens-like protrusion is 3 μm.

5. The protein-matrix microlens array diffraction device according to claim 1, wherein the height h of the microlens-like protrusion is 1 μm.

6. A method for preparing a protein-matrix microlens array diffraction device, comprising the following steps:
   (1) preparing a protein crystal, comprising:
      (1-1) mixing a protein solid with a solution having a concentration of a salt, comprising sodium chloride and sodium acetate, of 2% to 5% by mass to obtain a protein solution, wherein a mass fraction of the protein in the protein solution is 1 to 3 times a mass fraction of a saturated solution, and the protein solution is adjusted to have a pH of 4 to 6; and
(1-2) placing the protein solution obtained from step (1-1) in a container and leaving the protein solution to stand at a room temperature for a period of 6 to 24 h, wherein during the period water of the protein solution is naturally evaporated, thereby obtaining the protein crystal, and (2) emitting a femtosecond laser on a surface of the protein crystal obtained in step (1), wherein the femtosecond laser has a pulse duration of 35 to 120 fs, a single pulse energy of the femtosecond laser is half of a protein ablation threshold, and the femtosecond laser has a repetition frequency of 1 to 1000 Hz.

7. The method according to claim 6, wherein the protein solution is naturally evaporated at a temperature of 23° C. and a relative humidity of 30% for 24 h.

\* \* \* \* \*